ABSTRACT of US Patent 4,735,217

United States Patent [19]
Gerth et al.

[11] Patent Number: 4,735,217
[45] Date of Patent: Apr. 5, 1988

[54] DOSING DEVICE TO PROVIDE VAPORIZED MEDICAMENT TO THE LUNGS AS A FINE AEROSOL

[75] Inventors: Donald L. Gerth, Cincinnati; Delmar R. Muckenfuhs, Middletown, both of Ohio

[73] Assignee: The Procter & Gamble Company, Cincinnati, Ohio

[21] Appl. No.: 898,970

[22] Filed: Aug. 21, 1986

[51] Int. Cl.$^4$ .................................................. A24K 47/00
[52] U.S. Cl. ..................................... 131/273; 131/329; 128/203.17; 128/203.27; 128/204.17; 128/204.23
[58] Field of Search ...................... 131/273, 329, 330; 128/204.17, 203.17, 204.23, 203.27

[56] References Cited

U.S. PATENT DOCUMENTS

| | | |
|---|---|---|
| 239,196 | 3/1881 | Rousseaux . |
| 962,617 | 6/1910 | Bucceri . |
| 1,968,509 | 7/1934 | Tiffany ................................ 219/38 |
| 2,057,353 | 10/1936 | Whittemore, Jr. ................. 219/38 |
| 2,104,266 | 1/1938 | McCormick ....................... 131/330 |
| 2,342,853 | 2/1944 | Furstenberg ...................... 128/200 |
| 2,425,624 | 8/1947 | Lardinois ........................... 128/200 |
| 2,479,002 | 8/1949 | Ceperly .............................. 128/201 |
| 2,702,033 | 2/1955 | Pardeman .......................... 128/201 |
| 2,721,551 | 10/1955 | Lobl .................................... 128/208 |
| 2,764,154 | 9/1956 | Murai ................................. 128/201 |
| 2,809,634 | 10/1957 | Murai ................................. 128/195 |
| 2,830,597 | 4/1958 | Kummli .............................. 131/171 |
| 2,860,638 | 11/1958 | Bartolomeo ....................... 128/201 |
| 3,200,819 | 8/1965 | Gilbert ............................... 128/208 |
| 3,258,015 | 6/1966 | Ellis et al. .......................... 131/171 |
| 3,279,476 | 10/1966 | Noznick et al. ................... 131/10.7 |
| 3,313,305 | 4/1967 | Noznick et al. ................... 131/10.7 |
| 3,347,231 | 10/1967 | Chien-Hshuing Chang ..... 128/201 |
| 3,356,094 | 12/1967 | Ellis et al. .......................... 131/266 |
| 3,404,692 | 10/1968 | Lampert ............................. 131/170 |
| 3,683,936 | 8/1972 | O'Neil, Jr. ............................ 131/8 |
| 4,149,548 | 4/1979 | Bradshaw ....................... 131/170 A |
| 4,284,089 | 8/1981 | Ray .................................... 131/270 |
| 4,340,072 | 7/1982 | Bolt et al. .......................... 131/273 |
| 4,393,884 | 7/1983 | Jacobs ................................ 131/273 |
| 4,585,014 | 4/1986 | Fry ..................................... 131/175 |
| 4,585,015 | 4/1986 | Silberstein ......................... 131/339 |

Primary Examiner—V. Millin
Attorney, Agent, or Firm—E. Kelly Linman; John V. Gorman; Richard C. Witte

[57] ABSTRACT

A medicament dosing device capable of administering a vaporized medicament in the form of tiny aerosol particles to the mouth and lungs of the user at a substantially constant concentration level. In a particularly preferred embodiment the dosing device is used to provide nicotine to a cigarette smoker in a form and a dose that closely mimics a burning cigarette to satisfy the smoker's craving for nicotine, but without subjecting either the user or any non-users in the immediate vicinity to the tars and carbon monoxide of cigarette smoke. A preferred device comprises a battery powered resistance heater housed in a cigarette-shaped tube. A demand-operated switch is employed in the circuit so that as the user sucks air through the tube in a manner similar to puffing on a cigarette, energy is supplied to the resistance heater which vaporizes the nicotine. Because the system vaporizes the medicament being administered only upon activation of the demand-operated switch, the concentration of the medicament will be substantially constant each time the user sucks on the mouthpiece end of the cigarette-shaped tube, regardless of the length of the time intervals which pass between successive inhalations.

20 Claims, 3 Drawing Sheets

4,735,217

DOSING DEVICE TO PROVIDE VAPORIZED MEDICAMENT TO THE LUNGS AS A FINE AEROSOL

TECHNICAL FIELD

The present invention relates to a medicament dosing device capable of adminstering a vaporized medicament to the lungs of the user at a substantially constant concentration level.

The present invention further relates to such a dosing device which will provide nicotine to a cigarette smoker in a form and a dose that closely mimics a burning cigarette to satisfy the smoker's craving for nicotine, but without subjecting either the user or any non-users in the immediate vicinity to the tars and carbon monoxide of cigarette smoke.

The present invention has further relation to such a device to supply other vaporizable medicaments, such as menthol, to the lungs of the user in a very fine aerosol form at a substantially constant concentration level.

The present invention has still further relation to such a dosing device wherein the medicament being administered is vaporized only on demand in response to the user drawing a stream of cool air through the device, thereby causing the vaporized medicament to condense in a very fine aerosal with particles which are small enough to be dispersed throughout the user's lungs.

The present invention has still further relation to a self-contained, battery operated medicament dosing device which is approximately the size of a conventional cigarette, but which can be automatically actuated to vaporize the medicament without combustion by sucking on the mouthpiece end of the device.

BACKGROUND OF THE INVENTION

Inhalation devices for dosing various medicaments, including nicotine, are generally known in the art.

U.S. Pat. No. 3,258,015 issued to Ellis et al. on June 28, 1966 discloses a number of embodiments for a smoking device intended to provide dosing of nicotine without the inhalation of products of combustion normally encountered when smoking cigarettes. In most of the disclosed embodiments, an outer wrap of tobacco or similar combustible material is utilized to vaporize nicotine contained within a continuous passageway extending from the outermost end of the cigarette-like device to the mouthpiece end.

Most of the disclosed embodiments, while not requiring inhalation of smoke by the user, do require combustion of the outer wrap to provide the heat needed to vaporize the nicotine. However, the FIG. 9 embodiment of Ellis et al. discloses a smoking device utilizing a centrally located heating material comprised of pyrophorous material such as finely divided iron, nickel, zinc or lead of moderate activity. The centrally located tubular member is sealed to the atmosphere until such time as the user desires to operate the device. At this point a plug 64 is removed to expose the pyrophorous material to the atmosphere, thereby generating heat sufficient to vaporize nicotine contained in a nicotine releasable material 60 disposed outside the tubular member 61. The innermost end of the pyrophorous material containing tube is sealed by an impermeable disc 63 to prevent inhalation, while the user is allowed to draw the nicotine containing vapor from the concentric overwrap through the permeable disc 66 located near the mouthpiece end of the device. Once the heating process has been initiated with the device as disclosed in the U.S. Pat. No. 3,258,015 Ellis et al. patent, the nicotine will continue to be vaporized whether or not the user is drawing air through the passageway containing the nicotine. If the user allows long periods of time to elapse between successive inhalations, the concentration of nicotine vapor in the passageway can build up substantially. Thus the medicament concentration level encountered by the user with devices of the type described in the U.S. Pat. No. 3,258,015 Ellis et al. patent will vary greatly from one inhalation to the next, depending upon the time intervals between successive inhalations.

U.S. Pat. No. 3,356,094 issued to Ellis et al. on Dec. 5, 1967 discloses smoking devices somewhat similar to those disclosed in the U.S. Pat. No. 3,258,015 Ellis et al. patent. However, the devices disclosed in the U.S. Pat. No. 3,356,094 Ellis et al. patent require that a portion of the by-products of combustion which result from burning the tobacco surrounding the nicotine-containing passageway be drawn into the user's lungs. The devices shown in the U.S. Pat. No. 3,356,094 Ellis et al. patent differ from those disclosed in the U.S. Pat. No. 3,258,015 Ellis et al. patent in that they allow the user to better control the concentration level of the nicotine, i.e. drawing air through the tobacco containing portion of the device will accelerate its rate of combustion and hence the rate of vaporization of the nicotine in the central passageway. However, even the device disclosed in the U.S. Pat. No. 3,356,094 Ellis et al. patent does not give the user complete, on demand control over the concentration of vaporized nicotine developed in the interior pasageway. Furthermore, it suffers the disadvantage that it requires the user to inhale some of the harmful products of combustion in order to influence the rate of vaporization of the nicotine. This would certainly be undesirable in situations where the medicament in question is being administered to a person suffering from respiratory difficulties.

U.S. Pat. No. 3,200,819 issued to Gilbert on Aug. 17, 1965 discloses a smokeless, non-tobacco cigarette wherein a heating element, characterized as a vacuum tube, is energized by a small battery so as to heat flavored air as it passes from a flavor-containing cartridge 20 located at the outermost tip of the device to its mouthpiece end. However, the flavor-containing cartridge is not heated by the heating element and no means are provided for energizing and de-energizing the heat source on demand. Therefore the device disclosed in the patent to Gilbert would not function to administer a substantially constant concentration of a medicament which must be vaporized by the addition of heat.

U.S. Pat. No. 1,968,509 issued to Tiffany on July 31, 1934 and U.S. Pat. No. 2,057,353 issued to Whittemore, Jr. on Oct. 13, 1936 both disclose vaporizing units for liquid medicaments. These devices employ a resistance wire heating element energized by a battery which is activated by a manual switch. The device disclosed by Whittemore, Jr. further shows a wicking means to deliver the liquid medicament to the resistance heating wire. Neither of these device appears to be well suited for use in the user's mouth in the manner of a cigarette. In essence, they are portable vaporizing units powered by flashlight batteries which are controlled by manually operated "on/off" switches. Accordingly, the concentration of medicament vapor for any given inhalation by the user will depend upon: (a) how long the unit has been left in the "on" position immediately prior to inhaling the vapor; and (b) how long a period of time has passed since the preceding inhalation.

U.S. Pat. No. 2,809,634 issued to Murai on Oct. 15, 1957, U.S. Pat. No. 2,830,597 issued to Kummli on April 15, 1958 and U.S. Pat. No. 4,393,884 issued to Jacobs on July 19, 1983 all disclose inhalation devices which are automatically actuated by suction or manual pressure. However, the material to be inhaled from these devices is maintained in a pressurized form, usually as an aerosal. These devices would not function with non-aerosal medicaments which require the addition of heat for vaporization to occur.

While the aforementioned prior art devices have solved some of the problems associated with dosing of a vaporized or vaporizable medicament, none have simultaneously solved all of the difficulties normally encountered. Furthermore, none of these prior art devices have achieved a significant level of commercial acceptance, particularly as substitutes for conventional nicotine-containing cigarettes.

Accordingly, it is an object of the present invention to provide a dosing device for a vaporizable medicament which operates only on demand when the user draws air through the device.

It is another object of the present invention to provide such a dosing device which includes a self-contained power source and a heating element capable of vaporizing a medicament by the addition of heat only when the user draws air through the device.

It is another object of the present invention to provide such a device which is capable of delivering the vaporized medicament to the user in fine aerosal form at an approximately constant concentration level, regardless of the time interval which passes between successive inhalations.

It is still another object of the present invention to provide such a device which is combustion free, whereby neither the user nor any non-users in the immediate vicinity need inhale the harmful by-products of combustion in order to vaporize the medicament.

DISCLOSURE OF THE INVENTION

The present invention comprises a medicament dosing device capable of administering a vaporized medicament to the lungs of a user at a substantially constant concentration level. In a particularly preferred embodiment the dosing device is used to provide nicotine to a cigarette smoker in a form and a dose that closely mimics a burning cigarette to satisfy the smoker's craving for nicotine, but without subjecting either the user or any non-smokers in the immediate vicinity to the tars and carbon monoxide of cigarette smoke. The device preferably comprises a battery powered resistance heater housed in a cigarette-shaped tube. A demand-operated electrical switch is employed in the heating circuit so that as the user sucks air through the tube in a manner similar to puffing on a cigarette, energy is supplied to the resistance heater which vaporizes the nicotine. The vaporized nicotine condenses as a very fine aerosol in the cool air drawn through the device, thereby allowing tiny particles of the medicament to reach the alveolae of the user's lungs along with the air drawn through the device. Because the system vaporizes the medicament being administered only upon activation of the demand-operated electrical switch, the concentration of the medicament will be substantially constant each time the user sucks on the cigarette-shaped tube, regardless of the time intervals which pass between successive inhalations. Furthermore, because vaporization occurs only as air is being drawn across the medicament, nearly all of the vaporized medicament is effectively utilized by the user rather than merely re-condensing inside the device without reaching the user's lungs.

In a particularly preferred embodiment, the electrical air-flow actuated switch comprises a vane-type switch which is actuated by a resilient diaphragm located at the exterior end of the device. One or more air inlet orifices located about the periphery of the device near its diaphragm end allow the user to draw the incoming air across the vaporized medicament on its way to the user's mouth and lungs. The reduced pressure created inside the device when the user sucks on the mouthpiece end causes inward movement of the resilient diaphragm which contacts and closes the vane-type electrical switch against the battery. This completes the electrical circuit, thereby energizing the resistance heater on which the medicament is placed. Thus the medicament is vaporized only when air is drawn across its surface. While in the relatively cooler air stream, the vaporized medicament condenses to form tiny aerosal particles which are small enough to enter the user's lungs and be distributed throughout the alveolae thereof. Thus the medicament is effectively administered to the user's body through the lungs.

BRIEF DESCRIPTION OF THE DRAWINGS

While the specification concludes with claims particularly pointing out and distinctly claiming the present invention, it is believed the present invention will be better understood from the following description in conjunction with the accompanying drawings in which:

DETAILED DESCRIPTION OF THE INVENTION

FIGS. 1-5 disclose a particularly preferred medicament dosing device 10 of the present invention. In the illustrated embodiment, the dosing device 10 comprises a cylindrical body portion 15 joined to the mouthpiece end 25 by means of a conical section 20. The cylindrical body portion 15, the mouthpiece end 25 and the conical section 20 may be comprised of nearly any desired material, molded plastic being particularly preferred.

Figure 4:
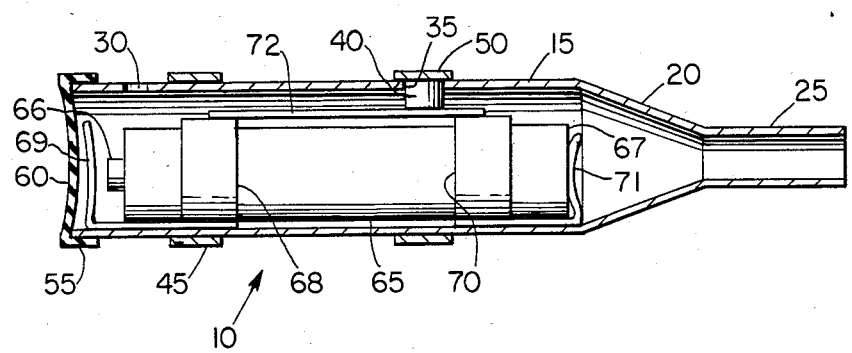
FIG. 4 is a greatly enlarged simplified cross-section of the device generally shown in FIG. 2 taken along section line 4—4 of FIG. 2.
Figure 5:
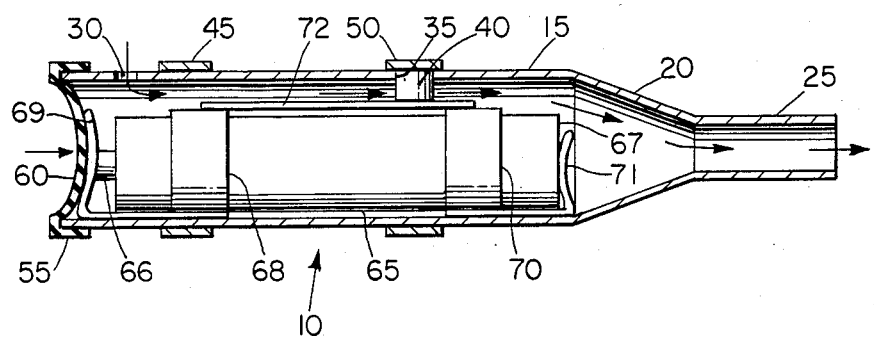
FIG. 5 is a greatly enlarged simplified cross-section of the device generally shown in FIG. 3 taken along section line 5—5 of FIG. 3.

As can best be seen from the cross-sections of FIGS. 4 and 5, the cylindrical body portion 15 has its exterior end closed by means of a resiliently deformable diaphragm member 55 which is preferably secured about the periphery of the cylindrical body portion 15 of the device. The diaphragm 55 preferably includes a centrally located deformable portion 60 which is substantially impermeable to the passage of air.

The cylindrical body portion 15 also includes at least one air inlet orifice 30 located near the exterior end of the device. As will be appreciated by those skilled in the art, a multiplicity of such orifices may, if desired, be employed. The resistance to air flow through orifice 30 is preferably adjustable by means of a sealing ring 45 which is axially slidable along the length of body portion 15. In the embodiment illustrated in FIGS. 1-5, the sealing ring 45 is not functioning to restrict air flow through orifice 30. However, depending upon the resistance desired by the user, the orifice 30 may be restricted by axially sliding sealing ring 45 in the direction of the exterior end of the device 10 to block at least a portion of orifice 30.

Figure 1:
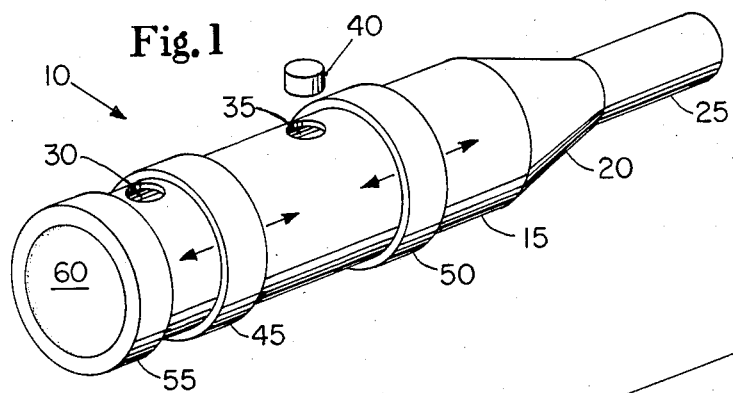
FIG. 1 is a simplified enlarged perspective illustration of a medicament dosing device of the present invention shown prior to insertion of the medicament pellet.
Figure 2:
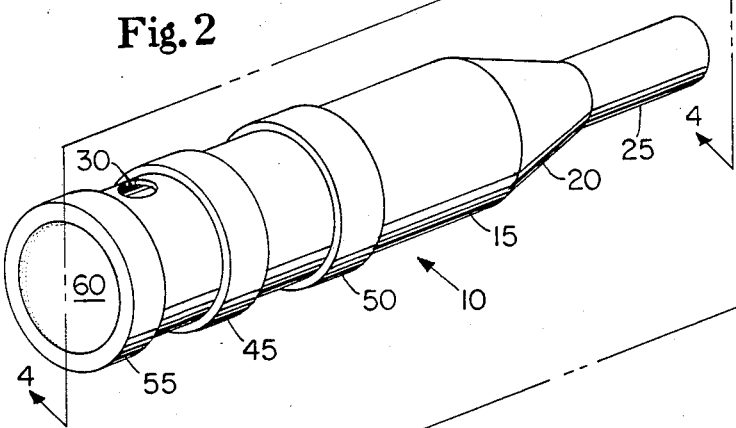
FIG. 2 is a view generally similar to that of FIG. 1, but showing the device after the medicament pellet has been inserted and the cylindrical restraining ring has been advanced along the axis of the device to cover the orifice through which the medicament pellet is inserted.
Figure 3:
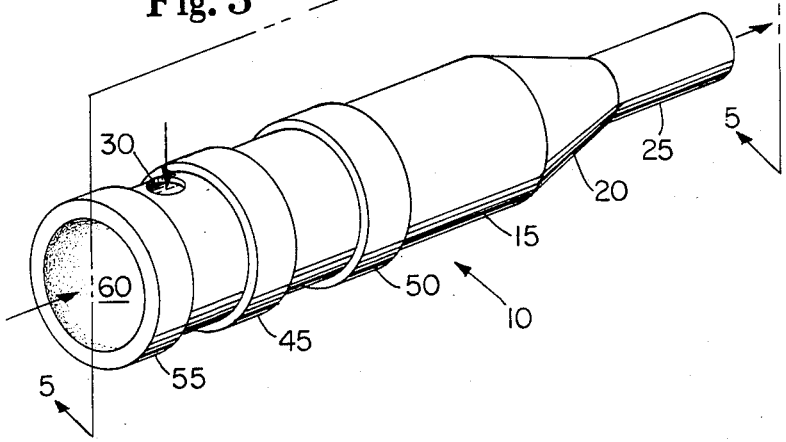
FIG. 3 is a view generally similar to that of FIGS. 1 and 2, but showing the condition of the resilient diaphragm in the end of the device when air is being drawn through the mouthpiece end.

A second orifice 35, also located in body portion 15, is preferably used for inserting a cylindrical pellet of vaporizable medicament 40 into position in the dosing device 10, as generally shown in FIGS. 1, 4 and 5. The pellet of vaporizable medicament 40 is preferably held in place by means of a restraining ring 50 generally similar to sealing ring 45, the restraining ring also being slidable along the axis of cylindrical body portion 15 of the dosing device 10. In the condition illustrated in FIG. 1, the restraining ring 50 is slid toward the mouthpiece end 25 to allow exposure of orifice 35 and insertion of the pellet of medicament 40. In the condition illustrated in FIGS. 2-5, the restraining ring 50 has been advanced to a position which blocks orifice 35, thereby preventing the pellet of vaporizable medicament 40 from being dislodged from the device 10.

Inside the cylindrical body portion 15 of the device there is also provided a self-contained electrical power source, as represented by battery 65. The positive end 66 of the battery 65 is fitted with a cylindrical metallic ring 68 having a deformable metallic vane or arm 69 in electrical contact with metallic ring 68. The negative end 67 of batter 65 is fitted with a similar metallic ring 70 having a spring tensioned metallic arm 71 maintained in electrical contact therewith. Metallic rings 68 and 70 are placed in electrical contact with one another by means of a resistance heating element 72 which has its opposite ends secured to metallic rings 68 and 70 so as to establish electrical continuity therebetween. The battery 65, metallic rings 68 and 70 and heating element 72 are secured within tubular body portion 15 of the device 10 by means well known in the art and therefore not shown (e.g. an adhesive). As can be seen from FIGS. 4 and 5, the heating element 72 is radially aligned with orifice 35, and the pellet of vaporizable medicament 40 has a height sufficient to cause slight deformation of heating element 72 when restraining ring 50 is advanced into the position shown in FIGS. 4 and 5. This ensures good contact between the medicament 40 and the heating element 72.

The cross-section of FIG. 4 shows the de-energized condition of the electrical circuit when no air is being sucked through the mouthpiece end 25 of the device 10. Because there is no contact between metallic arm 69 and the positive end 66 of battery 65, the electrical circuit which includes the resistance heating element 72 is in an "open" condition. Accordingly, no current flows through resistance heating element 72 and there is no melting or vaporization of the pellet of medicament 40.

The cross-section of FIG. 5 depicts the condition which exists when the user sucks air through the mouthpiece end 25 of the device. In particular, air is drawn in through orifice 30 in cylindrical body portion 15 of the device. This air travels along the interior passageway of cylindrical body portion 15, around the pellet of medicament 40, through conical section 20 and mouthpiece end 25 and into the user's mouth and lungs, as generally shown by the arrows in FIG. 5. Sucking on the mouthpiece end 25 of the device also reduces the pressure existing within the device relative to the surrounding atmosphere. When this occurs, the deformable diaphragm 55 is acted upon by the surrounding atmospheric pressure so that its movable portion 60 is caused to exhibit an inwardly concave conformation, as generally shown in FIG. 5. This inward movement of portion 60 of diaphragm 55 causes movable metallic arm 69 to move into contact with the positive end 66 of battery 65. This completes or "closes" the electrical circuit which includes the resistance heating element 72 shown generally in FIGS. 4 and 5. It is, of course, recognized that different types of air flow actuated switches could be used in lieu of the diaphragm actuated switch illustrated in the Drawing Figures e.g, a vane switch. The particular switch selected is unimportant so long as it reliably actuates in response to the flow of air through the device.

The heat produced by resistance heating element 72 elevates the temperature of the pellet of medicament 40 sufficiently to cause at least some vaporization of the medicament. Because the relatively cool air being drawn through orifice 30 is being drawn across the pellet of medicament 40 on its way to the user's mouth, a substantial portion of the vaporized medicament is picked up by the moving air stream and carried to the mouthpiece end 25 of the device and ultimately into the user's mouth and lungs. While in the relatively cooler air stream, the vaporized medicament condenses to form tiny aerosol particles which are small enough to enter the user's lungs and be distributed to the alveolae thereof. This is a necessary condition for the medicament to be effectively administered to the user's body through the lungs. Without the moving airstream, the vaporized medicament will merely condense inside the device and will never reach the user's lungs.

As will be appreciated by those skilled in the art, when the air ceases to flow through the device 10, i.e., when the user stops sucking on the mouthpiece end 25, the movable portion 60 of resiliently deformable diaphragm 55 will return to its substantially undistorted condition, as generally shown in FIG. 4. This allows the spring loaded metallic arm 69 to return to its normal at rest position as generally shown in FIG. 4, thereby breaking or "opening" the electrical circuit which includes resistance heating element 72. Accordingly, the resistance heating element 72 immediately begins to cool and vaporization of the pellet of medicament 40 ceases as soon as its temperature has dropped below the vaporization temperature of the particular medicament being administered. This prevents the vapor concentration from building up inside the device during the time intervals which elapse between successive inhalations from the mouthpiece end 25 of the device.

Figure 6:
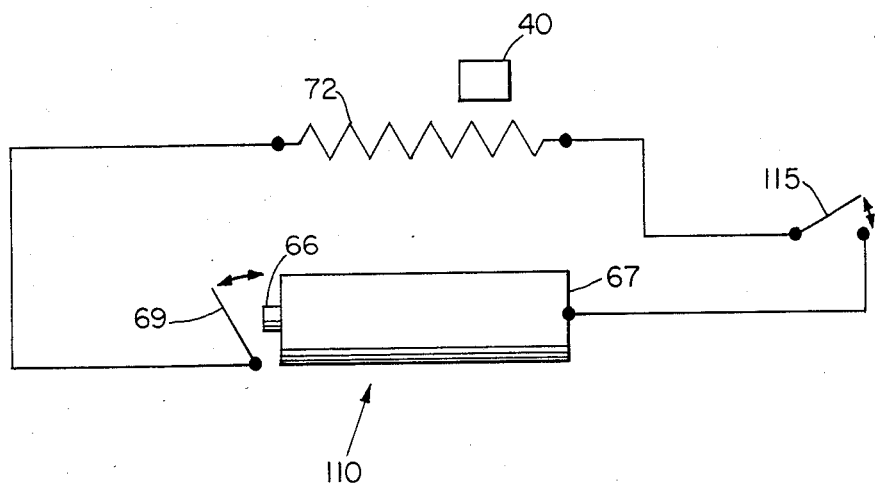
FIG. 6 is an electrical schematic of an alternative embodiment of the present invention.

FIG. 6 is a simplified electrical schematic of an alternative embodiment 110 of the present invention. Embodiment 110 can be very similar to embodiment 10 shown in FIGS. 1-5 with the exception that a normally "open" pressure actuated switch 115 is added to the mouthpiece end of the device. If the user wishes to keep the device 110 in his or her mouth without inhaling vaporized medicament with each breath of air drawn through the device, the pressure responsive switch 115 is actuated by pressure applied by the user's mouth or lips, as generally shown in the electrical schematic of FIG. 6. Such a pressure actuated switch 115 could be calibrated to permit the heating circuit to be turned "on" only when the user's lips apply a predetermined threshold pressure sufficient to close switch. The normally open pressure actuated switch 115 must, of course, be connected in series with the air flow actuated switch 69 and battery 65 so that both switches must be closed before vaporization of the medicament 40 can occur. Thus, pressure must be applied to the pressure actuated switch 115 and air must flow through the device to close the air flow actuated switch 69 before any power is supplied to the heating element 72. So long as the pressure actuated switch 115 remains "open", the user can draw non-medicated air through the device and into his or her lungs without energizing the heating element.

Since vaporization of medicament 40 occurs only upon a demand for air through dosing devices of the present invention, the vapor concentration level in the air stream drawn into the user's mouth and lungs remain substantially constant for any given air flow rate through the device, regardless of the interval of time which passes between successive draws. This not only minimizes waste of the medicament pellet 40, but also enables the user to administer the medicament within a substantially given concentration range. In a particularly preferred embodiment, the vapor concentration level of the medicament can be adjusted upwardly or downwardly as desired by increasing or decreasing the air flow through orifice 30 via movement of sealing ring 45 along the tubular body portion 15 of the device. This ability to control vapor concentration level may be particularly important for medicaments which are effective for their intended purpose only when administered within a predetermined concentration range or which, for one reason or another, may be harmful to the user if a certain maximum concentration level is exceeded.

EXAMPLE

An exemplary dosing device of the present invention was made utilizing transparent acrylic plastic tube stock. The body portion of the device had an exterior diameter of approximately 2.5 centimeters and overall length of approximately 8 centimeters. The inside diameter of the body portion was approximately 1.9 centimeters.

The mouthpiece end of the device comprised a similar piece of plastic tube stock measuring approximately 1.9 centimeters in outside diameter by approximately 3 centimeters long. The inside diameter of the mouthpiece end measured approximately 1.2 centimeters in diameter. The smaller mouthpiece end was forced inside the large body portion tube and secured in substantially sealed relation thereto by the resultant interference fit. An EverReady ® alkaline type E91 (AA) battery, as available from Union Carbide, having a rating of 1.5 volts DC and capable of delivering a current of about 2.0 amps during each 2 second puff on the device was utilized as the power source. The heating element comprised a Nichrome ® (241 alloy) segment, as available from Driver-Harris Co. of Harrison, N.J. It measured approximately one inch long by ⅛ inch wide by 0.001 inches thick and exhibited a resistance of approximately 0.50 ohms. The opposite ends of the heating element were soldered to metallic rings 68 and 69.

The configuration and orientation of the battery 65, the metallic rings 68 and 70, the metallic arms 69 and 71 and the resistance heating element 72 were essentially as shown in the cross-sections of FIGS. 4 and 5. The diaphragm 55 comprised a resilient fingertip cut from a rubber glove and secured about the periphery of the large diameter plastic tubing, as generally shown in FIGS. 4 and 5. The air intake orifice 30 measured approximately 0.8 millimeters in diameter, and the orifice 35 utilized to load the medicament pellet 40 measured approximately 4 millimeters in diameter.

The test medicament was comprised of a menthol pellet measuring approximately 3.9 millimeters in diameter by 5 millimeters in height.

The exemplary device was user activated by sucking on the mouthpiece end. An inhalation of approximately 35 milliliters volume over a two second duration was utilized to test the device. The medicament pellet comprised of menthol having a melting point of 108° F. and a boiling point of 218° F. emitted vapor as the Nichrome heating element 72 achieved a temperature in the range of 190°-220° F. within the 2 second duration. Based on organoleptic perception of the user, the device appeared to provide a substantially constant concentration of menthol vapor in the air drawn across the heated menthol pellet over the life of the device. The particular battery tested was capable of providing heating element temperatures in the 200° F. range for about 5 cycles, each cycle having an overall duration of approximately ten minutes. Each ten minute cycle was carried out using a continuously repeating pattern of two seconds "on" and 58 seconds "off" in an attempt to emulate the behavior of a cigarette smoker.

Although the exemplary device described in the preceding paragraphs was tested only with menthol, it is believed that similar results can be obtained working with nicotine-containing compounds. For example, it is believed that liquid nicotine base ($C_{10}H_{14}N_2$), which is colorless and volatile and which turns brown and acquires a tobacco-like odor upon exposure to air, could be mixed with a solid such as menthol to form a pellet of nicotine-containing medicament 40. Alternatively, a nicotine tartrate or a mixture of nicotine and citric acid could be produced as a solid or semi-solid and used in a manner similar to the menthol pellet described above to provide dosing of nicotine at safe levels comparable to those experienced when smoking a cigarette, but without the harmful by-products of combustion. It is also believed feasible to coat the heating element 72 with a nicotine-containing compound in lieu of using a vaporizable pellet 40. Such easily replaceable, coated heating elements could be used as an alternative to vaporizable pellets and a non-disposable heating element, as disclosed herein.

While particular embodiments of the present invention have been illustrated and described, it will be obvious to those skilled in the art that various changes and modifications can be made without departing from the spirit of the scope of the invention. It is intended to cover in the appended claims all such modifications that are within the scope of this invention.

What is claimed is:

1. A medicament dosing device capable of automatically administering a vaporized medicament in the form of tiny aerosol particles to the mouth and lungs of a user at a substantially constant concentration level for any given air flow rate through the device regardless of the time interval which passes between successive inhalations, said device comprising:
   (a) an element having an elongated body portion of a size to be carried and manipulated in the hand of a user, said element including a mouthpiece at one end of said body portion for insertion in the mouth of the user, the opposite outermost end of said body portion projection outwardly from the user's mouth;
   (b) a medicament releasing composition which releases medicament vapor when subject to an elevated temperature below its ignition point disposed in said body portion of said element;
   (c) combustion-free heating means for heating the medicament releasing composition to an elevated temperature below its ignition point so as to cause the release of medicament vapor disposed in said body portion of said element;
   (d) a continuous passageway from the outer end of said body portion of said element to said mouthpiece end and communicating with the medicament releasing composition; and
   (e) normally open switch means disposed within said body portion of said element, said normally open switch means being automatically held closed only in response to the user drawing air through said passageway from said outermost end of said body portion of said element to said mouthpiece end, said switch means being electrically connected to said heating means so as to energize said heating means to vaporize said medicament only while air is being drawn through said passageway by the user, a substantial portion of said medicament which is vaporized being entrained within said air drawn through said passageway, whereby for any given air flow rate through said device the concentration level of said vaporized medicament contained therein will be substantially constant regardless of the time interval which passes between successive inhalations.

2. The device of claim 1, wherein said combustion-free heating means comprises a resistance element connected in series with a battery.

3. The device of claim 2, wherein said switch means comprises a diaphragm actuated switch, said diaphragm actuated switch being electrically connected in series with said battery and said resistance element.

4. The device of claim 2, wherein said medicament releasing composition comprises a coating applied to the surface of said resistance element.

5. The device of claim 2, wherein said medicament releasing composition comprises a solid which is placed in contact with said resistance element.

6. The device of claim 4 or claim 5, wherein said medicament releasing composition comprises nicotine and said medicament vapor comprises nicotine vapor.

7. The device of claim 6, wherein said medicament releasing composition comprises nicotine tartrate.

8. The device of claim 6, wherein said medicament releasing composition comprises a mixture of nicotine and citric acid.

9. The device of claim 6, wherein said medicament releasing composition comprises a mixture of nicotine and menthol.

10. The device of claim 1, wherein said medicament releasing composition comprises menthol and said medicament vapor comprises menthol vapor.

11. A medicament dosing device capable of automatically administering a vaporized medicament in the form of tiny aerosol particles to the mouth and lungs of a user at a substantially constant concentration level for any given air flow rate through the device regardless of the time interval which passes between successive inhalations, said device comprising:
   (a) an element having an elongated body portion of a size to be carried and manipulated in the hand of a user, said element including a mouthpiece end at one end of said body portion for insertion in the mouth of the user, the opposite outermost end of said body portion projecting outwardly from the user's mouth;
   (b) housing means for containing a medicament releasing composition which releases medicament vapor when subjected to an elevated temperature below its ignition point, said housing means being disposed in said body portion of said element;
   (c) combustion-free heating means for heating the medicament releasing composition contained in said housing means to an elevated temperature below its ignition point so as to cause the release of medicament vapor disposed in said body portion of said element;
   (d) a continuous passageway from the outer end of said body portion of said element to said mouthpiece end and communicating with the medicament releasing composition contained in said housing means; and
   (e) normally open switch means disposed within said body portion of said element, said normally open switch means being automatically held closed only in response to the user drawing air through said passageway from said outermost end of said body portion of said element to said mouthpiece end, said switch means being electrically connected to said heating means so as to energize said heating means to vaporize said medicament contained in said housing means only while air is being drawn through said passageway by the user, a substantial portion of said medicament which is vaporized being entrained within said air drawn through said passageway, whereby for any given air flow rate through said device the concentration level of said vaporized medicament contained therein will be substantially constant regardless of the time interval which passes between successive inhalations.

12. The device of claim 11, wherein said combustion-free heating means comprises a resistance element connected in series with a battery.

13. The device of claim 12, wherein said switch means comprises a diaphragm actuated switch, said diaphragm actuated switch being electrically connected in series with said battery and said resistance element.

14. The device of claim 12, wherein said housing means for containing said medicament releasing composition comprises an orifice in said body portion of said element, said orifice being located adjacent said resistance element, whereby any medicament releasing composition placed in said housing means is maintained in contact with said resistance element.

15. The device of claim 11, including means for adjusting the resistance to air flow through the passageway connecting the outer end of said element and said mouthpiece end.

16. The device of claim 15, wherein said means for adjusting the resistance of air flow through said passageway comprises at least one air inlet orifice in the outer end of said body portion of said element and means for obstructing said air inlet orifice to any desired degree.

17. The device of claim 16, wherein said means for obstructing said air inlet orifice to any desired degree comprises an air-impervious sealing ring surrounding said body portion of said element and axially slidable along the length of said body portion in the area of said air inlet orifice, whereby said air inlet orifice can be obstructed to any desired degree by advancing said air-impervious sealing ring across said air inlet orifice in said body portion.

18. A medicament dosing device capable of automatically administering a vaporized medicament in the form of tiny aerosal particles to the mouth and lungs of a user at a substantially constant concentration level for any given air flow rate through the device regardless of the time interval which passes between successive inhalations, said device comprising:
   (a) an element having an elongated body portion of a size to be carried and manipulated in the hand of a user, said element including a mouthpiece end at one end of said body portion for insertion in the mouth of the user, the opposite outermost end of said body portion projecting outwardly from the user's mouth;
   (b) housing means for containing a medicament releasing composition which releases medicament vapor when subjected to an elevated temperature below its ignition point, said housing means being disposed in said body portion of said element;
   (c) combustion-free heating means for heating the medicament releasing composition contained in said housing means to an elevated temperature below its ignition point so as to cause the release of medicament vapor disposed in said body portion of said element;
   (d) a continuous passageway from the outer end of said body portion of said element to said mouthpiece end and communicating with the medicament releasing composition contained in said housing means;
   (e) first normally open switch means disposed within said body portion of said element, said first normally open switch means being automatically held closed only in response to the user drawing air through said passageway from said outermost end of said body portion of said element to said mouthpiece end; and
   (f) second normally open switch means disposed within said mouthpiece end of said element, said second normally open switch means being held closed in response to the application of pressure thereto by the user's lips when said mouthpiece end of said device is inserted into the user's mouth, said first normally open switch means and said second normally open switch means being electrically connected in series with one another and with said heating means so as to energize said heating means to vaporize said medicament contained in said housing means only while pressure is maintained on said first normally open switch means and air is being drawn through said passageway by the user, a substantial portion of said medicament which is vaporized being entrained within said air drawn through said passageway, whereby for any given air flow rate through said device the concentration level of said vaporized medicament contained therein will be substantially constant regardless of the time interval which passes between successive inhalations.

19. The device of claim 18, wherein said first air flow actuated switch means comprises a diaphragm actuated switch.

20. The device of claim 18, wherein said first air flow actuated switch comprises a vane switch.

* * * * *

UNITED STATES PATENT AND TRADEMARK OFFICE
CERTIFICATE OF CORRECTION

PATENT NO. : 4,735,217
DATED : April 5, 1988
INVENTOR(S) : DONALD L. GERTH and DELMAR R. MUCKENFUHS It is certified that error appears in the above-identified patent and that said Letters Patent is hereby corrected as shown below:

Column 1, line 40, after "of" insert -- different --.

Claim 1, column 9, line 13, after "mouthpiece" insert -- end --.

Claim 1, column 9, line 17, "projection" should read -- projecting --.

Claim 1, column 9, line 19, "subject" should read -- subjected --.

Claim 16, column 11, line 9, "of" should read -- to --.

Signed and Sealed this

Twenty-third Day of August, 1988

Attest:

DONALD J. QUIGG

Attesting Officer

Commissioner of Patents and Trademarks